United States Patent [19]

Hartdegen et al.

[11] 4,195,127

[45] * Mar. 25, 1980

[54] PROCESS FOR IMMOBILIZING PROTEINS

[75] Inventors: Frank J. Hartdegen, Columbia; Wayne E. Swann, Pasadena, both of Md.

[73] Assignee: W. R. Grace & Co., New York, N.Y.

[*] Notice: The portion of the term of this patent subsequent to Jul. 4, 1995, has been disclaimed.

[21] Appl. No.: 851,932

[22] Filed: Nov. 16, 1977

Related U.S. Application Data

[60] Division of Ser. No. 743,035, Nov. 18, 1976, Pat. No. 4,098,645, which is a continuation-in-part of Ser. No. 660,982, Feb. 24, 1976, abandoned, which is a continuation-in-part of Ser. No. 585,674, Jun. 10, 1975, abandoned.

[51] Int. Cl.$^2$ .......................... C07G 7/00; C07G 7/02
[52] U.S. Cl. ........................................ 435/174; 260/8; 260/112 R; 435/182
[58] Field of Search .................. 195/63, 68, DIG. 11; 260/6, 8, 112 R; 424/78, 85, 94

[56] References Cited

U.S. PATENT DOCUMENTS

| 3,672,955 | 6/1972 | Stanley | 195/68 |
| 3,905,923 | 9/1975 | Klug | 195/63 X |
| 3,975,350 | 8/1976 | Hudgin et al. | 424/78 X |

FOREIGN PATENT DOCUMENTS 2413137 10/1975 Fed. Rep. of Germany .
953414 3/1964 United Kingdom .

*Primary Examiner*—David M. Naff
*Attorney, Agent, or Firm*—Philip M. Pippenger

[57] ABSTRACT

A protein which can be an enzyme is immobilized by: (a) admixing the protein and an isocyanate-capped liquid polyurethane prepolymer to form an intermediate product; and (b) foaming the intermediate product by reacting it with water to form a polyurethane foam comprising the immobilized enzyme.

11 Claims, No Drawings

PROCESS FOR IMMOBILIZING PROTEINS

This application is a divisional of U.S. Patent application Ser. No. 743,035, filed Nov. 18, 1976, now U.S. Pat. No. 4,098,645, which in turn is a continuation-in-part of U.S. Ser. No. 660,982, filed Feb. 24, 1976, now abandoned, which is in turn a continuation-in-part of U.S. Ser. No. 585,674, filed June 10, 1975, now abandoned.

BACKGROUND OF THE INVENTION

1. Field of the Invention

This invention relates to proteins. More particularly, it relates to an immobilized protein. Even more particularly, this invention relates to: (a) such a protein which has been immobilized by contacting it with an excess of an isocyanate-capped liquid polyurethane prepolymer to form a mixture which is cured by contacting it (the mixture) with an amount of water effective for immobilizing the protein; and (b) to the process whereby such protein is immobilized. Still more particularly, this invention relates to such protein and such process where said protein is an enzyme, an antibody, or an antigen.

It is noted that the immobilized (bound) proteins of our invention are formed by reacting a solution comprising an isocyanate-capped liquid polyurethane prepolymer and the protein with water to produce a self-supporting foam comprising: (a) the immobilized protein; and (b) poly(urea-urethane) moieties.

2. Description of the Prior Art

A review of enzyme technology was published in the Aug. 18, 1975 issue of Chemical & Engineering News (pp. 22–41); although not prior art with respect to the instant invention, said review is of interest. Chemical & Engineering News is published by the American Chemical Society.

U.S. Pat. No. 3,574,062 (195/63, Sato) teaches a method for preparing a bound protein (an enzyme) wherein a polyester polyurethane is diazotized with a diazonium salt of an amino acid and then coupled with a nonenzymatic animal protein to form a diazotized polyurethane which is reacted with an enzyme to form the immobilized enzyme.

U.S. Pat. No. 3,705,084 (195/63, Reynolds) teaches a flow-through enzyme reactor comprising: (a) a macroporous reactor core; (b) a polymeric surface (which can be a polyurethane resin) on the reactor core; (c) an enzyme adsorbed on the polymeric surface and crosslinked in place thereon by a difunctional agent (e.g., a polyisocyanate).

Reynolds prepares the immobilized enzyme for his reactor by adsorbing an active enzyme on a polymeric surface and further immobilizing the enzyme by crosslinking it in place with a crosslinking agent such as a monomeric polyisocyanate.

German Offenlegungsschrift No. 2,319,706 published Nov. 15, 1973 teaches an enzyme bound to a polyurethane foam and a method for preparing such bound enzyme.

U.S. Pat. No. 3,791,927 (195/63, Forgione et al) teaches a water-insoluble bound protein (enzyme) entrapped within the cells of a self-supporting reticulated cellular material (which can be a polyurethane foam), the protein (enzyme) being bound to the cellular material.

U.S. Pat. No. 3,672,955 (195/68, Stanley) teaches a process for preparing a bound protein (enzyme) comprising: (a) emulsifying an aqueous dispersion of the enzyme with a solution of a polyisocyanate in a volatile water-immiscible solvent (e.g., methylchloroform); (b) admixing the resulting emulsion with a solid particulate carrier; and (c) evaporating the solvent therefrom. Stanley's polyisocyanate can be an isocyanate-capped liquid polyurethane prepolymer. Said U.S. Pat. No. 3,672,955, in its entirety, is incorporated herein by reference.

It is noted that, in his Example 3, Stanley reports the binding of an enzyme component (a peroxidase) of a fermentation broth by admixing a portion of the broth with a polyisocyanate dissolved in methylchloroform. It seems probably that, under Stanley's reaction conditions, any other enzymes which were present in the broth would have been immobilized (rendered insoluble in water, i.e., bound).

Silman et al, Annual Review of Biochemistry, 1966, 35 (Part 2), pages 873–908 presents a review of methods for preparing water-insoluble derivatives of enzymes, antigens, and antibodies.

Singer, Nature, 1959, 183, 1523–1524 teaches a method for reacting a protein with a diisocyanate (m-xylene diisocyanate).

U.S. patent application Ser. No. 250,012, filed May 3, 1972, and now abandoned (Wood et al, inventors) which is assigned to W. R. Grace & Co. teaches, in Example 21, a foamed polyurethane comprising an immobilized enzyme (urease), a method for preparing such immobilized enzyme, and a method for using it.

Said application Ser. No. 250,012 also teaches, e.g., in claim 8, a foamable composition comprising: (a) an isocyanate-capped polyurethane prepolymer; (b) water; and (c) biostats, fungicides, or enzymes. A similar teaching occurs in claim 7 of the abovementioned German Offenlegungsschrift No. 2,319,706.

U.S. Pat. No. 3,929,574, Wood et al, teaches the preparation of a bound (immobilized) protein, an enzyme, by a process comprising contacting an isocyanate-capped liquid polyurethane prepolymer with an aqueous dispersion of the enzyme under foam-forming conditions, whereby the polyurethane foams and the enzyme becomes integrally bound to the resulting polyurethane foam.

It is noted that, in said U.S. Pat. No. 3,929,574, Wood et al reports, in Example 1, that an enzyme (cellulase) present in a fermentation broth was immobilized (bound or rendered insoluble) by admixing the broth with an isocyanate-capped liquid polyurethane prepolymer under conditions which produced a foam. It seems probable that, under the conditions of said Example 3, any other enzymes present in the broth would have been immobilized.

U.S. Pat. No. 3,905,923 (260/2.5 AD, Klug) teaches an immobilized enzyme system formed from an enzyme and a hydrophilic poly(urea-urethane) foam, the foam surrounding, entrapping, and supporting the enzyme in an active configuration. The hydrophilic foam is formed by the reaction of water with a hydrophilic isocyanate-capped polyoxyalkylene prepolymer.

Isocyanate-capped polyurethane prepolymers are well known to those skilled in the art. See, for example: (a) the penultimate paragraph on page 854 of Volume 9 of the Second Edition of the Kirk-Othmer "Encyclopedia of Chemical Technology", John Wiley and Sons, Inc., New York, N.Y.; or (b) the third full paragraph in the left hand (first) column of page 872 of the Second Edition of "The Encyclopedia of Chemistry", George L. Clark, Editor, Reinhold Publishing Corporation, New York, N.Y.

T. Richard and N. F. Olson, "Immobilized Enzymes in Food and Microbial Processes", Plenum Press, New York, N.Y., 1974, pages 35–36 teach the formation of a bound (immobilized) enzyme by reacting the enzyme, water, and a polyisocyanate polymer.

Weetall, Journal of Bacteriology, volume 93, pages 1876–1880 (1967) teaches the isolation and purification of large quantities of bacterial specific antibodies by using polymerized microorganisms as a specific immunoadsorbent. The microorganisms were polymerized by reaction with tetrazotized benzidine.

SUMMARY OF THE INVENTION

In summary this invention is directed to an improvement in a process for preparing an immobilized or bound protein (which can be an enzyme, an antibody, an antigen, or any other protein) comprising admixing an isocyanate-capped liquid polyurethane prepolymer, the protein, and water to produce a polyurethane foam (a poly(urea-urethane) foam) with the protein integrally bound to the polyurethane foam, the improvement comprising: (a) admixing the prepolymer and the protein in the absence of water to form a resulting solution; and (b) foaming and polymerizing the resulting solution by admixing it with an amount of water effective for foaming the intermediate product, i.e., the resulting solution (e.g., 0.5–3 or 0.9–2 parts of water per part of said liquid polyurethane prepolymer plus the protein which was admixed to form the resulting solution) at a temperature effective for producing foaming (e.g., room temperature, or somewhat lower, or somewhat higher).

The process is conducted at a temperature at which the isocyanate-capped liquid polyurethane prepolymer exists in the liquid state and at a temperature below the denaturation temperature of the protein which is being immobilized.

DESCRIPTION OF PREFERRED EMBODIMENTS

In preferred embodiments of the process recited in the above Summary:

1. The foam comprising the bound (immobilized i.e., insoluble) protein is washed (preferably with water) to remove unbound protein and to hydrolyze any unreacted isocyanate groups.

2. The isocyanate-capped liquid polyurethane prepolymer is prepared by reacting toluene diisocyanate and a polyethylene glycol.

3. The isocyanate-capped liquid polyurethane prepolymer is prepared by reacting toluene diisocyanate and a polyethylene glycol having a molecular weight (average molecular weight) of about 800–1,200 (preferably about 1,000).

4. The isocyanate-capped liquid polyurethane prepolymer is prepared by reacting toluene diisocyanate and a member selected from the group consisting of a polyoxybutylene polyol polymer, ethylene glycol, diethylene glycol, a polyoxyethylene polyol polymer, pentaerythritol, glycerol, trimethylol propane, and a polyoxypropylene polyol polymer.

5. The protein is an enzyme, an antibody, or an antigen.

6. The isocyanate-capped liquid polyurethane prepolymer is prepared by reacting toluene diisocyanate with an admixture of a polyethylene glycol having an average molecular weight of about 800–1,200 (preferably about 1,000) and trimethylolpropane, the trimethylolpropane and the polyethylene glycol being provided in a mole ratio of about 1:1–4 and the toluene diisocyanate being provided at a rate of about 0.85–1.25 (preferably 0.95–1.1) mole of toluene diisocyanate per equivalent (17 g) of —OH provided by the polyethylene glycol plus the trimethylolpropane.

7. The isocyanate-capped liquid polyurethane prepolymer can be prepared from toluene diisocyanate and ethylene glycol according to the method recited in Example 1 of above-mentioned U.S. Pat. No. 3,929,574 (Wood et al). Said patent in its entirety is incorporated herein by reference.

In another preferred embodiment ("Embodiment A") this invention is directed to the resulting solution prepared as described in the above Summary - including the preferred embodiments thereunder. It is believed that said solution comprises a reaction product resulting from a reaction of some of the isocyanate groups of the isocyanate-capped liquid polyurethane prepolymer with at least a portion of protein molecules which are admixed with said isocyanate-capped prepolymer. However, we do not wish to be bound by theory and/or belief.

In another preferred embodiment ("Embodiment B") this invention is directed to a process for preparing an immobilized protein which can be an enzyme, an antibody, or an antigen, said process comprising:

(a) forming a first product by admixing, in the absence of water, the protein and a liquid polyisocyanate (e.g., at least one of the liquid polyisocyanates listed in Table 1, infra, or the like);

(b) forming a second product comprising an isocyanate-capped liquid polyurethane prepolymer with the protein dissolved therein by admixing and reacting, in the absence of water, the first product and an amount of a polyol effective for forming the second product (the polyol can be at least one of those listed in Table 2, infra, or the like and can include at least one of those recited in the paragraph immediately preceding said Table 2); and (c) forming the immobilized protein by admixing the second product and an amount of water effective for producing foaming.

In an another preferred embodiment ("Embodiment C") this invention is directed to a process for preparing an immobilized protein which can be an enzyme, an antibody, or an antigen, said process comprising:

(a) forming a first product by admixing, in the absence of water, the protein and a liquid polyol (the polyol can be at least one of those listed in Table 2, infra, or the like and can include at least one of those recited in the paragraph immediately preceding said Table 2);

(b) forming a second product comprising an isocyanate-capped liquid polyurethane prepolymer with the protein dissolved therein by reacting, in the absence of water, the first product and an amount of a polyisocyanate effective for forming the second product (the polyisocyanate can be at least one of those listed in Table 1, infra, or the like); and (c) forming the immobilized protein by admixing the second product and an amount of water effective for producing foaming.

In the methods of Embodiments B and C it is generally preferred to use about 2–500 or 50–100 mg of protein per gram of polyol. The ratio of polyisocyanate to polyol plus enzyme must be such that an amount of isocyanate groups effective for reacting with water to produce foaming is present in the second product of said Embodiments B and C. Generally about 1.25-4.5 or 1.8-2.2 milliequivalents of —NCO per gram of second product is preferred.

In another preferred embodiment ("Embodiment D") this invention is directed to an improvement in a process for preparing an immobilized enzyme, said process comprising admixing an isocyanate-capped liquid polyurethane prepolymer, the enzyme, and water to produce a polyurethane foam with the enzyme integrally bound to the polyurethane foam, the improvement comprising:

(a) admixing, in the absence of water, the liquid polyurethane prepolymer and a substrate reactable with the enzyme to form a first composition;

(b) admixing, in the absence of water, the first composition and the enzyme to form a second composition; and (c) foaming the second composition by admixing it with an amount of water effective for producing foam to form a poly(urea-urethane) foam comprising the immobilized enzyme.

In the process of Embodiment D it is generally preferred to use about 5-100 moles or 8-12 moles of substrate per mole of enzyme.

In another perferred embodiment ("Embodiment E") this invention is directed to a protein-containing foam comprising about 0.1 to 50% by weight of an active protein preparation on an anhydrous basis and a hydrophilic poly(urea-urethane) foam matrix having an oxyalkylene backbone containing at least 50 mole percent oxyethylene; said hydrophilic foam being formed by reacting a solution consisting essentially of said protein dissolved in an isocyanate-terminated prepolymer (an isocyanate-capped liquid polyurethane prepolymer) with water and said hydrophilic foam entrapping and supporting said protein in an active configuration for biological activity, said protein can be selected from the group consisting of an enzyme, an antibody, and an antigen.

DETAILED DESCRIPTION OF THE INVENTION

In the process of our invention the isocyanate-capped liquid polyurethane prepolymer acts as: (a) a solvent to dissolve the protein which is to be bound; and (b) a reactant to react with the protein to bind it (the protein) to the poly(urea-urethane) foam which results when the aforesaid resulting solution is admixed with water to form said foam.

The solidification temperature of the isocyanate-capped liquid polyurethane prepolymer used in our process will vary depending on the molecular weight of the prepolymer and on the structure of the backbone of the prepolymer.

The thermal denaturation temperature of proteins is generally above about 35° C. However, some proteins are stable for relatively short periods (e.g., 5-30 minutes or longer) at higher temperatures (e.g., at temperatures up to about 70° C. or somewhat higher).

It is generally preferred to use about 2-10 or more (e.g., up to 100-1000 or more) times the stoichiometric amount of isocyanate-capped liquid polyurethane prepolymer where forming the product of Embodiment A (which is identical with the intermediate product of the above Summary). This intermediate product can be foamed in a subsequent step—by admixing with water as in the above Summary—to produce a protein intimately bound to the polyurethane foam.

This invention is directed to a process for immobilizing (binding) proteins in active and reusable form to a polyurethane foam. A polyurethane prepolymer is produced in the known way by the reaction of an excess of di- and tri- isocyanates and other polyisocyanates (including mixtures of polyisocyanates) with compounds containing active hydrogen, particularly glycols, polyglycols, polyester polyols, polyether polyols, other polyols, and mixtures of two or more such polyols. This reaction produces an isocyanate-capped liquid polyurethane prepolymer. The protein and said prepolymer are admixed in the absence of water to form a resulting solution which is then admixed and reacted with water to form a poly(urea-urethane) foam comprising the immobilized or bound protein which is chemically and-/or biologically active.

The formation of the resulting solution (step "(a)" of the above Summary) is conducted in the absence of water. Said step "(a)" can be conducted in the presence or absence of a diluent or in the presence of a mixture of diluents. Because of our disclosure, it will be readily apparent to those skilled in the art that a diluent which would denature the protein or prevent or substantially reduce foaming during the above-mentioned foaming step cannot be present. Diluents which are operable include but are not limited to those taught by Stanley (U.S. Pat. No. 3,672,955). The diluents can be very soluble in water, e.g., acetone and the like; moderately soluble in water, e.g., methyl acetate, methyl ethyl ketone, and the like; or insoluble in water, e.g., benzene and the other diluents listed in the paragraph starting on line 45, of column 1, of Stanley's above-mentioned U.S. Pat. No. 3,672,955. Said U.S. Pat. No. 3,672,955, in its entirety, is incorporated herein by reference.

Diluents serve to reduce the viscosity of: (a) the isocyanate-capped liquid polyurethane prepolymer; and (b) the resulting mixture.

The foaming step (step "(b)" of the above Summary) can also be conducted in the absence of a diluent or in the presence of one or more of such diluents (i.e., the above-mentioned diluents). However, where conducting said foaming step in the presence of a diluent care must be exercised to avoid the presence of so much diluent that the viscosity of the mixture comprising diluent and the resulting solution of the above Summary plus the water admixed therewith to produce foaming is not reduced to an extent that carbon dioxide produced by the reaction of water and isocyanate groups fails to produce foaming or produces insufficient foaming to form a self-supporting poly(ureaurethane) foam comprising the immobilized protein.

Where the diluent is insoluble or substantially insoluble in water, an emulsifying agent can be used during the foaming step. Stanley (U.S. Pat. No. 3,672,955) teaches the use of such emulsifying agent.

The binding (protein immobilizing) reaction is a general one applicable to all proteins including, but not limited to, enzymes, antibodies, and antigens. For example, the following can be bound: urease, cellulase, pectinase, papain, bromelain, chymotrypsin, trypsin, ficin, lysozyme, glucose isomerase, lactase, penicillin amidase, human immunoglobulin G, invertase, asparginase, and the like. We have found no enzyme, antibody or antigen, or other protein which cannot be bound. The purity of the protein is not critical. Binding (protein immobilization) can be accomplished using: (a) pure crystalline protein; (b) partially purified non-crystalline protein; (c) impure dried extracts containing enzyme, antibody, or antigen activity; or (d) unpurified dried extract from a fermentation broth (e.g., an acetone precipitation product obtained from the broth). Our work shows that our process can be used to bind proteins (including enzymes, antibodies, and antigens) of substantially any purity.

Following formation of the protein/prepolymer solution certain proteins will cause the prepolymer to solidify if the protein is present in sufficiently large amounts. An example of this phenomena is penicillin amidase. Where the amidase level exceeds about 10 weight percent based on the weight of the prepolymer, the prepolymer solution exhibits increased viscosity and cannot be stirred after about 60 minutes. At concentrations below about 5 weight percent, the solution can still be stirred and admixed with water to give foams.

It has been discovered that the solidified penicillin amidase polyurethanes are biologically active, i.e. the enzyme is bound in active form. For example, 100 mg of prepolymer 3 (see Example 12, infra), 100 mg of penicillin amidase and 10 mg of penicillin G (Na salt) were admixed to form a solution. During admixing the viscosity of the solution increased until after about 10 minutes following contacting of the reagents, the solution could no longer be stirred by hand. After one hour the solution was a hard solid material which was ground and screened to yield particles less than 840 micrometers in size. On a dry weight basis the activity of the particles was 1020 units/g. Activity was defined as the micromoles of penicillin G split per minute at 30° C. at pH 8.

It is believed that other proteins will react with the prepolymer to form biologically active solid polymers, assuming the proteins are present in the prepolymer solution in large enough amounts. Presently, there is no way to determine in advance which protein will react with the prepolymer to form solids or at what levels the proteins must be employed in the solution. However, given the basic discovery of the present invention, i.e. that protein/prepolymer solutions can be formed without destroying the biological activity of the protein, for any protein, solid formation can be determined simply by dissolving the protein at successively larger levels in different batches of prepolymer. Given the teachings of the present invention the above test can easily be performed by one of ordinary skill in enzyme chemistry. Once it is decided to immobilize a particular protein in active form by binding it to a polyurethane matrix, it is a simple matter to form solutions using increasingly large levels of protein as solute and determine if solid formation occurs. Conversely, if solid formation is to be avoided the above test can also be performed to determine the maximum binding level of proteins.

The above-mentioned U.S. Pat. No. 3,672,955 teaches that proteins (enzymes) can be bound to isocyanate-capped polyurethanes. In the process of said patent the ioscyanate-capped polyurethane is dissolved in a water-immiscible solvent. This solution is emulsified, using an emulsifying agent, in the presence of an active enzyme which is dispersed in water.

Our process is similar in some respects to that of Stanley's said U.S. Pat. No. 3,672,955. We can use the same isocyanate-capped polyurethane prepolymer (which that patent refers to as polyisocyanates); we can use the same polyols (to prepare our prepolymer); and we can use the same enzymes. As in that patent (although we do not wish to be bound to any particular theory) the mechanism is apparently the reaction of one or more amine and/or hydroxyl groups on the protein with one or more isocyanate groups on the polyurethane prepolymer molecule.

As in the Stanley patent, our isocyanate-capped liquid polyurethane prepolymers can be prepared by reacting a polyol with a polyisocyanate using an excess of the isocyanate to ensure the presence of free (unreacted) isocyanate groups on the polyurethane prepolymer molecules.

Our process is also similar in some respects to that of the above-mentioned U.S. Pat. No. 3,929,574 (Wood et al). We can use the same isocyanate-capped polyurethane prepolymer (which that application refers to as an isocyanate-capped polyurethane), and we can use the same proteins (enzymes). As in said U.S. Pat. No. 3,929,574 our process is directed to preparing a protein bound to a polyurethane foam.

However, unlike the process of said U.S. Pat. No. 3,929,574, we admix our prepolymer and our enzyme under substantially water-free conditions. Said application admixes its prepolymer with an aqueous dispersion of an enzyme.

Thus, in the process of said Wood et al patent, the admixing and foaming are conducted in one step while in our process there are two steps. These are:

1. An admixing step wherein the protein (which can be an enzyme) and the prepolymer are mixed in the absence of water to form a resulting solution.

2. A foaming step wherein water is admixed with the previously prepared resulting solution to produce the foam having the protein bound thereto (i.e., the poly(urea-urethane) comprising the immobilized enzyme.

In our process (see our examples, infra) a very much greater portion of the protein is bound to the foamed polyurethane (i.e., present in the poly(urea-urethane) foam in an active but water-insoluble form) than is the case in the process of said patent. In other words, our process makes much more efficient use of the protein than does the process of said patent.

Any liquid polyurethane prepolymer, including those taught by said U.S. Pat. No. 3,929,574, which contains at least two free isocyanate groups per prepolymer molecule is suitable for binding proteins in accordance with this invention. We prefer that the prepolymer contain an average of two isocyanate groups per molecule. An even higher ratio can be used, for example, 2-8 isocyanate groups per polyurethane molecule. Ratios higher than this are operable, but offer no advantage. Any excess isocyanate groups left in the polyurethane foam (after binding of the enzyme) will be destroyed by hydrolysis upon the first contact of the foam with water, for example, during a washing step preliminary to use of the bound enzyme.

The isocyanate-capped (isocyanate-terminated) liquid polyurethane prepolymers used in this invention contain at least two isocyanate groups (reactive isocyanate groups) per molecule of prepolymer. An isocyanate-capped polyurethane prepolymer is a "liquid polyurethane prepolymer" if: (a) it is a free flowing liquid at 40°–70° C.; or if it will dissolve in an inert solvent (e.g., an inert solvent such as those listed supra including those taught by Stanley) to form a solution containing about 1–50% (or 10–25%) by weight of isocyanate-capped polyurethane prepolymer.

As used herein, the term "liquid isocyanate-capped polyurethane prepolymer" means a liquid polyurethane or polyurea molecule containing at least about two free isocyanate groups per molecule.

Representative examples of polyisocyanates which can be reacted with an active hydrogen containing compound (e.g., a glycol, polyol, polyglycol, polyester polyol, polyether polyol, and the like) to make an isocyanate-capped polyurethane in accordance with the invention include those listed in Table 1.

TABLE 1 toluene-2,4-diisocyanate
toluene-2,6-diisocyanate
commercial mixtures of toluene-2,4- and 2,6-diisocyanates
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
3,3'-dichloro-4,4'-biphenylene diisocyanate
1,6-hexamethylenediisocyanate
1,4-tetramethylene-diisocyanate
1,10-decamethylenediisocyanate
1,5-naphthalenediisocyanate
cumene-2,4-diisocyanate
4-methoxy-1,3-phenylenediisocyanate
4-chloro-1,3-phenylenediisocyanate
4-bromo-1,3-phenylenediisocyanate
4-ethoxy-1,3-phenylenediisocyanate
2,4'-diisocyanatodiphenylether
5,6-dimethyl-1,3-phenylenediisocyanate
2,4-dimethyl-1,3-phenylenediisocyanate
4,4'-diisocyanatodiphenylether
benzidinediisocyanate
4,6-dimethyl-1,3-phenylenediisocyanate
9,10-anthracenediisocyanate
4,4'-diisocyanatodibenzyl
3,3'-dimethyl-4,4'-diisocyanatodiphenylmethane
2,6-dimethyl-4,4'-diisocyanatodiphenyl
2,4-diisocyanatostilbene
3,3'-dimethyl-4,4'-diisocyanatodiphenyl
3,3'-dimethoxy-4,4'-diisocyanatodiphenyl
1,4-anthracenediisocyanate
2,5-fluorenediisocyanate
1,8-naphthalenediisocyanate
2,6-diisocyanatobenzfuran
2,4,6-toluenetriisocyanate
p,p',p''-triphenylmethane triisocyanate A useful class of liquid isocyanate-capped polyurethane prepolymers are those derived from polyether polyols and polyester polyols. These compounds may be prepared, as is well known in the art, by reacting a polyether (or polyester) polyol with a polyisocyanate, using an excess of the latter to ensure provision of free isocyanate groups in the product. A typical, but by no means limiting, example is illustrated in idealized equation form below:

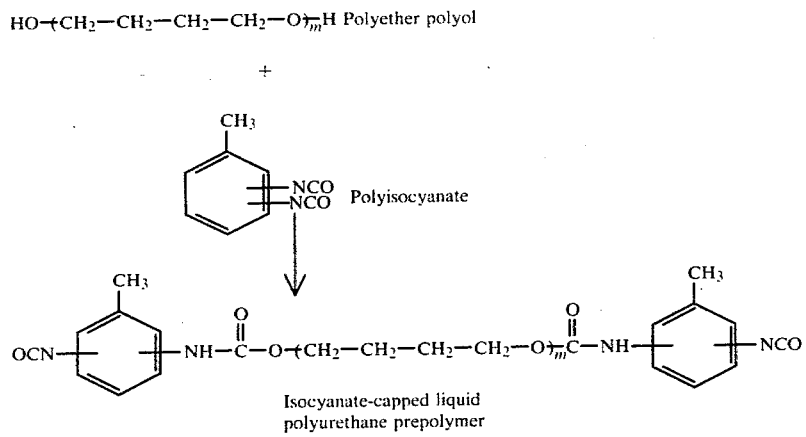

(In the above formulas, m represents the number of tetramethyleneether repeating units. This may range, for example, about from 5 to 50.)

The compounds useful for the purposes of the invention may be prepared by reacting any of the aboveexemplified polyisocyanates with any of a wide variety of polyols including: (a) simple polyols such as those listed in Table 2, infra; and (b) polyether polyols and polyester polyols. Representative examples of these polyols are described below.

Among the polyether polyols which may be so used are those prepared by reaction of an alkylene oxide with an initiator containing active hydrogen groups, a typical example of the initiator being a polyhydric alcohol such as ethylene glycol; a polyamine such as ethylene diamine; phosphoric acid, etc. The reaction is usually carried out in the presence of either an acidic or basic catalyst. Examples of alkylene oxides which may be employed in the synthesis include ethylene oxide, propylene oxide, any of the isomeric butylene oxides, and mixtures of two or more different alkylene oxides such as mixtures of ethylene and propylene oxides. The resulting polyether polyols contain a polyether backbone and are terminated by hydroxyl groups. The number of hydroxyl groups per polymer molecule is determined by the functionality of the active hydrogen initiator. For example, a difunctional alcohol such as ethylene glycol (as the active hydrogen initiator) leads to polyether chains in which there are two hydroxyl groups per polymer molecule. When polymerization of the oxide is carried out in the presence of glycerol, a trifunctional alcohol, the resulting polyether molecules contain an average of three hydroxyl groups per molecule. Even higher functionality—more hydroxyl groups—is obtained when the oxide is polymerized in the presence of such polyols as pentaerythritol, sorbitol, sucrose dipentaerythritol, and the like. In addition to those listed above, other examples of polyhydric alcohols which may be reacted with alkylene oxides to produce useful polyether polyols include those listed in Table 2.

TABLE 2 propylene glycol
trimethylene glycol
1,2-butylene glycol
1,3-butanediol
1,4-butanediol
1,5-pentanediol
1,2-hexylene glycol
1,10-decanediol
1,2-cyclohexanediol
2-butene-1,4-diol
3-cyclohexene-1,1-dimethanol
4-methyl-3-cyclohexene-1,1-dimethanol
3-methylene-1,5-pentanediol
diethylene glycol
(2-hydroxyethoxy)-1-propanol
4-(2-hydroxyethoxy)-1-butanol
5-(2-hydroxypropoxy)-1-pentanol
1-(2-hydroxymethoxy)-2-hexanol
1-(2-hydroxypropoxy)-2-octanol
3-allyloxy-1,5-pentanediol
2-allyloxymethyl-2-methyl-1,3-propanediol
[(4-pentyloxy)methyl]-1,3-propanediol
3-(o-propenylphenoxy)-1,2-propanediol
thiodiglycol
2,2'-[thiobis(ethyleneoxy)]diethanol
polyethyleneether glycol (molecular weight about 200)
2,2'-isopropylidenebis(p-phenyleneoxy)diethanol
1,2,6-hexanetriol
1,1,1-trimethylolpropane
3-(2-hydroxyethoxy)-1,2-propanediol
ethylene glycol
3-(2-hydroxypropoxy)-1,2-propanediol
2,4-dimethyl-2-(2-hydroxyethoxy)methylpentanediol-1,5
1,1,1-tris[(2-hydroxyethoxy)methyl]ethane
1,1,1-tris[(2-hydroxypropoxy)methyl]propane
triethanolamine
triisopropanolamine
resorcinol
pyrogallol
phloroglucinol
hydroquinone
4,6-di-tertiarybutyl catechol
catechol
orcinol
methylphloroglucinol
hexylresorcinol
3-hydroxy-2-naphthol
2-hydroxy-1-naphthol
2,5-dihydroxy-1-naphthol
bis-phenols such as 2,2-bis(p-hydroxyphenyl)propane and bis-(p-hydroxyphenyl)methane
1,1,2-tris-(hydroxyphenyl)ethane
1,1,3-tris-(hydroxyphenyl)propane An especially useful category of polyether polyols are the polytetramethylene glycols. They are prepared by the ring-opening polymerization of tetrahydrofuran, and contain the repeating unit.

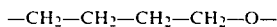

in the polymer backbone. Termination of the polymer chains is by hydroxyl groups.

Also especially desirable are the polyoxyethylene polyols HO$-(-CH_2CH_2-O)_x$H in which x is an average number such that the polyol has an average molecular weight of up to about 1000 (or about 2000 or somewhat higher).

The polyester polyols which may be employed as precursors are most readily prepared by condensation polymerization of a polyol with a polybasic acid. The polyol and acid reactants are used in such proportions that essentially all the acid groups are esterified and the resulting chain of ester units is terminated by hydroxyl groups. Representative examples of polybasic acids for producing these polymers are oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, α-hydromuconic acid, β-hydromuconic acid, α-butyl-α-ethylglutaric acid, α, β-diethylsuccinic acid, o-phthalic acid, isophthalic acid, terephthalic acid, hemimellitic acid, trimellitic acid, trimesic acid, mellophanic acid, prehnitic acid, pyromellitic acid, citric acid, benzenepentacarbosylic acid, 1,4-cyclohexane dicarboxylic acid, diglycollic acid, thiodiglycollic acid, dimerized oleic acid, dimerized linoleic acid, and the like. Representative examples of polyols for forming these polymers include ethylene glycol, 1,3-propylene glycol, 1,2-propylene glycol, 1,4-butylene glycol, 1,3-butylene glycol, 1,2-butylene glycol, butene-1,4 diol, 1,5-pentane diol, 1,4-pentane diol, 1,3-pentane diol, 1,6-hexane diol, hexene-1,6-diol, 1,7-heptane diol, diethylene glycol, glycerine, trimethylol propane, 1,3,6-hexanetriol, trimethanolamine, pentaerythritol, sorbitol, and any of the other polyols listed hereinabove in connection with the preparation of polyether polyols.

On being intimately contacted with a protein such as an enzyme, antibody, antigen, or the like, an isocyanate-capped polyurethane prepolymer becomes chemically very active. Some of the free isocyanate groups of the prepolymer are believed to react with the amine groups of the protein, and subsequently when water is added, some isocyanate groups react with water to give carbon dioxide and to form amine groups on the polyurethane molecule. These latter amine groups react with free isocyanate groups on neighboring polyurethane molecules, and this reaction (forming a urea linkage) will cause formation and growth of a poly(urea-urethane) polymer and will also introduce cross links between the polymer molecules. This further growth and cross linking is essential for the formation of a good foam. We believe (but do not wish to be bound by theory) that our superior results (i.e., the binding of a substantially greater portion of the added enzyme than is obtained in the prior art) is because of reaction between the protein and the isocyanate groups of a liquid isocyanate-capped polyurethane prepolymer in the absence of a competing reaction between the water and the isocyanate groups of the prepolymer in the resulting solution of step (a) of our Summary. In the prior art water and unbound protein (protein which has not yet had an opportunity to react with the prepolymer) are present at the same time and the competing reactions (i.e., reaction between the protein and the prepolymer on the one hand and water and the prepolymer on the other hand) proceed simultaneously thereby to compete with each other. As noted, supra, in our process the protein is added before the water is added.

Other additives such as crosslinking agents (polyamines, polythiols, polyacids) surfactants, wetting agents, antifoaming agents, dyes, antioxidants, fillers, etc., may also be present during foaming.

It is, of course, the release of the carbon dioxide that provides gas for foam formation.

The ratio of protein to isocyanate-capped liquid polyurethane prepolymer is not critical. However, it is important that said ratio be such that all of the isocyanate groups of the prepolymer are not consumed by reaction with the protein, thereby to leave unreacted isocyanate groups available to react with water to form carbon dioxide. It is the thus liberated carbon dioxide which causes the foaming that results in the formation of the foamed polyurethane (to which the protein is bound).

The ratio of water to protein plus isocyanate-capped liquid polyurethane prepolymer is not critical; however, we generally prefer to use about 0.5–3 or 0.9–2 parts by weight of water per part by weight of said prepolymer plus protein.

Bound enzymes prepared by the method of this invention are useful in analytical chemistry. For example, urea can be determined by passing a solution of urea through a column packed with urease bound to a polyurethane foam to quantitatively convert the urea to ammonia which can be determined by titration or by a colorimetric procedure.

Invertase bound to the polyurethane foam can be used to convert sucrose to invert sugar.

Lipase bound to the polyurethane foam can be packed in a column. Organic esters can be hydrolyzed (converted to their "parent" alcohol and organic acid) by passing a mixture of water and ester through the packed column. The acid and alcohol components can then be separated and recovered by conventional techniques. This procedure can also be used to analyze mixtures of esters.

Numerous other uses for bound enzymes prepared by the method of our invention will be readily apparent to those skilled in the art.

Bound antigens prepared by the method of this invention are useful for removing antibodies from biological samples. For example, as recited infra, bound human immunoglobulin G (IgG), an antigen, is useful for removing rheumatoid arthritis factor (an antibody) from human blood.

Bound antibodies prepared by the method of this invention are useful for removing antigens from biological samples. For example, the antibody of hepatitis can be bound to a polyurethane foam according to the process of this invention, and the resulting bound antibody can be used to remove the hepatitis antigen from blood (e.g., blood in blood banks).

The bound protein of this invention can be used in a batch system or in a continuous system. One method for operating a batch system is illustrated by a procedure for hydrolyzing urea present in an aqueous system. In this method one or more pieces of foamed polyurethane (i.e., our self-supporting poly(urea-urethane) foam) with the enzyme (urease) bound thereto is placed in a batch of aqueous urea to be hydrolyzed to ammonia. When the hydrolysis is completed the particles of bound enzyme are removed from the hydrolyzed sample, washed if desired, and placed in another batch of aqueous urea which is to be hydrolyzed.

However, we may prefer to use our bound protein in a manner wherein the foam with the protein bound thereto is packed into a column and the solution to be treated is passed through the column. This can be done in a fully continuous manner—for example for hydrolyzing (inverting) sucrose solution with bound invertase. This can also be done in a batch manner—for example where determining urea by hydrolyzing a plurality of urea solution to ammonia with bound urease and determining the amount of urea in each sample by analyzing the hydrolyzed sample (solution exit the packed column) for ammonia. Where using this method after each sample has been passed through the packed column the column is washed with water and the wash water and hydrolyzed urea solution (ammonia solution) are combined and the ammonia content of the combined liquor and wash water is determined.

The bound protein of this invention has a long service life. For example:

1. Where the bound protein is an enzyme it does not lose its activity even where used for hundreds of hours.

2. Where the bound protein is an antigen (useful for removing an antibody from an aqueous system) it will become spent ("saturated") when it has taken up an equivalent amount of antibody. It then becomes necessary to regenerate the bound protein (i.e., to free it of antibody). This can be done by passing an aqueous regenerating solution through the packed column and washing the regenerating solution from the regenerated column. An aqueous glycine hydrochloride solution (for example, 0.15–3 molar, preferably about 0.5 molar) is an excellent regenerating solution. Such glycine hydrochloride solution has a pH of about 2.5.

3. Where the bound protein is an antibody (useful for removing an antigen from an aqueous system) it will become spent (saturated) when it has taken up an equivalent amount of antibody. It then becomes necessary to regenerate the bound protein (i.e., to free it of antigen). This can be done by passing an aqueous regenerating solution such as the above described glycine hydrochloride solution through the packed column and washing the regenerated column as above.

Enzymes of all types can be bound by the process of this invention. Such enzymes include:

oxido reductases
transferases
hydrolases
lyases
isomerases
ligases.

Typical of the specific enzymes which can be immobilized (i.e., bound) according to the process of this invention are listed in Table 3.

TABLE 3 urease
trypsin
lactase
glucose oxidase
chymotrypsin
ribonuclease
peroxidase
pepsin
rennin
invertase
papain
asparaginase
pectinase
pectin esterase
penicillin amidase
glucose isomerase
lysozyme
amino acid acylase pronase
alcohol dehydrogenase
α-amylase
β-amylase
subtilisin
amino acid oxidase
catalase
tannase
phenol oxidase
glucoamylase
pullulanase
cellulase
ficin
bromelain
pancreatin
isoamylase
lipase
malic dehydrogenase
hexokinase
lactate dehydrogenase
adenosine deaminase
uricase
galactose oxidase
diaphorase
cholinesterase
aldolase
pyruvate carboxylase
phospharylase
cephalosporin amidase
isocitric dehydrogenase
α-glycerolphosphate dehydrogenase
glyceraldehyde-3-phosphate dehydrogenase
malic enzyme
glucose-6-phosphate dehydrogenase
5-dehydroshikimic reductase
glutathione reductase
glycolic acid oxidase
yeast cytochrome c reductase
luciferase
nitrite reductase
glutamyl transferase
glutathione synthetase
glycocyamine phosphokinase
hippuric acid synthetase
aldehyde oxidase
succinic dehydrogenase
nitrate reductase
xanthine oxidase
lipoyl dehydrogenase
flavin peroxidase
glycine oxidase
carboxylase
α-keto acid dehydrogenase
transketolase.

The instant invention will be better understood by referring to the following specific but nonlimiting examples and procedures. It is understood that said invention is not limited by these examples and procedures which are offered merely as illustrations; it is also understood that modifications can be made without departing from the spirit and scope of the invention.

The examples were actually run.

The procedures, while not actually run, illustrate certain embodiments of our invention.

EXAMPLE 1

An isocyanate-capped liquid polyurethane prepolymer was prepared by reacting 2 milliequivalents (meq), 1 g, of a polyethylene glycol having an average molecular weight of 1000 with 2.63 meq, 0.229 g, of toluene diisocyanate. The resulting prepolymer was designated "Prepolymer No. 1".

A replication of the above procedure was repeated wherein said procedure was modified by using 20 meq of the polyethylene glycol and 26.3 meq of the toluene diisocyanate. The resulting isocyanate-capped liquid polyurethane prepolymer was designated "Prepolymer No. 1-A".

EXAMPLE 2

An admixture was prepared by admixing 1 g of Prepolymer No. 2 described in Example 9, infra, and 100 milligrams (mg) of human immunoglobulin G (IgG). The IgG dissolved and the resulting solution was stirred for 15 minutes in a dry atmosphere at ca. 25° C. Then a 2 g portion of water was added to said solution at ca. 25° C. while stirring. The resulting water-containing system began to foam and within 10 minutes foam formation was complete. The resulting foam was thoroughly washed with water. The wash water was collected and analyzed for IgG by ultraviolet spectrophotometry. It was found that less than 1% of the IgG initially charged was washed out of the foam by the wash water. In other words, 99% of the IgG originally charged was bound to the polyurethane foam. The washed foam with the IgG bound thereto was designated "Foam A".

EXAMPLE 3

Foam A was packed into a column. Human blood containing 100 mg of rheumatoid arthritis factor was slowly passed through the packed column. The red blood cells were not lysed. Analysis of the blood exit the column showed that substantially all of the rheumatoid arthritis factor had been removed therefrom.

A second portion of human blood containing about 100 mg of rheumatoid arthritis factor was slowly passed through the same column. Only a small portion of the rheumatoid arthritis factor was removed from this sample of blood showing the the activity of the bound protein was exhausted.

The bound protein was reactivated by passing about 100 ml of a glycine hydrochloride solution (ca. 0.5 molar having a pH of 2.5) through the packed column. The packed column was washed free of glycine hydrochloride with water. A third portion of human blood containing about 100 mg of rheumatoid arthritis factor was slowly passed through the packed column. Analysis of the blood exit the column showed that all of the rheumatoid arthritis factor had been removed therefrom. This establishes the fact that the bound IgG had been reactivated by treating with the glycine hydrochloride.

The bound IgG can be reactivated for use in a very large number of runs—15-20 or more.

EXAMPLE 4

(Comparative Run)

This run was made to show the superiority of our process for preparing protein bound to polyurethane over the prior art process.

A 1 g portion of liquid isocyanate-capped polyurethane prepolymer (Prepolymer No. 2) prepared in Example 9 was admixed with a composition prepared by admixing 100 mg of human IgG with 2 g of water. The resulting mixture of prepolymer, IgG, and water was stirred for about 10 minutes. In about another 5 minutes foaming was complete. The foam was thoroughly washed with water and the washings were analyzed as above. It was found that 35% of the charged IgG was present in the wash water.

It was found that the bound IgG prepared in this example was effective for removing rheumatoid arthritis factor from human blood without lysing the red-blood cells. However it would only remove about 65% of the amount that was removed by the bound IgG prepared in Example 2, supra, before requiring regeneration by treatment with glycine hydrochloride solution.

EXAMPLE 5

A polyurethane-bound protein was prepared according to the general method of Example 2. However, in this instance the enzyme invertase was bound to a polyurethane using the general procedure of Example 2 except that invertase was substituted for IgG and Prepolymer No. 3 prepared in Example 12 was substituted for Prepolymer No. 2.

It was found that 91% of the enzyme (invertase) was bound to the polyurethane foam (poly(urea-urethane) foam).

The resulting bound enzyme was highly effective for inverting sucrose solutions. This enzyme activity was retained through many (1440) hours wherein sucrose solution was continuously passed through a column packed with the bound invertase. At the end of this time the bound enzyme still retained all of its original activity.

EXAMPLE 6

(Comparative Run)

When the method of Example 5 was modified by admixing the enzyme (invertase) with the water and then adding the enzyme-water mix to the prepolymer, only 68% of the charged enzyme was bound to the polyurethane. The remainder of the charged enzyme (42% thereof) was found in the wash water obtained by washing the foamed polyurethane having the enzyme bound thereto with water.

EXAMPLE 7

Asparaginase was bound to polyurethane foam using the general method of Example 5 wherein said asparaginase was substituted for the invertase. In this instance 75% of the enzyme (asparaginase) was bound to the foam. The bound enzyme was found to be highly active and it retained its activity during 12 batch assays with one hour washes between assays where used to convert asparagine (an amide) to aspartic acid.

EXAMPLE 8

(Comparative Run)

When the method of Example 7 was repeated but modified by admixing the enzyme (asparaginase) with the water before admixing the enzyme and isocyanate-capped polyurethane prepolymer, no enzyme was bound to the resulting foam. All of the enzyme was washed from the foam by the wash water, and the washed foam had no enzymatic activity.

Thus Example 7, supra, where compared with Example 8, shows the superiority of the process of our invention.

EXAMPLE 9

Two moles of a polyethylene glycol having an average molecular weight of 1,000 (PEG 1,000) and one mole of trimethylolpropane (TMP) were admixed and dried at 100°-110° C. under a pressure of 5-15 Torr to remove water. The resulting dried mixture, which contained a total of 7 moles (119 g) of reactive terminal hydroxyl (—OH) groups, was slowly added (taking about an hour) to a vessel containing 6.65 moles of toluene diisocyanate (TDI) while stirring the TDI and the resulting mixture. The TDI and the resulting mixture in the vessel were maintained at 60° C. The resulting mixture was stirred for 3 hours, while maintaining it at about 60° C., after all of the PEG 1,000-TMP mixture had been added to the reaction vessel. Then an additional 1.05 mole of toluene diisocyanate was added and stirring was continued for an additional hour while maintaining the stirred mixture at about 60° C. Thus, a 10 molar percent excess of the TDI was added to the PEG 1,000-TMP mixture. This assured that all hydroxyl groups of the polyols (the PEG 1,000 plus the TMP) were capped with isocyanate and that some chain extension occurred because of crosslinking of the polyols with the excess TDI.

The resulting liquid isocyanate-capped polyurethane prepolymer which resulted was designated "Prepolymer No. 2". Prepolymer No. 2 can be used for protein binding according to the process of this invention.

The physical properties of foams having proteins bound thereto can be varied by varying the ratios of the polyols used to prepare the isocyanate-capped liquid polyurethane prepolymer used in our process. The physical properties can also be varied by substituting other polyols (e.g., those selected from the list of polyols presented, supra).

EXAMPLE 10

An admixture was prepared using 1 gm of Prepolymer No. 2 and 5 mg of fungal lactase at about 25° C. The resulting first mixture was stirred for 15 minutes at about 25° C. in a dry atmosphere. Then a 2 g portion of water was added to the first mixture while stirring the resulting second mixture at about 25° C. The resulting second mixture began to foam, and within 10 minutes foam formation was complete. The resulting foam was thoroughly washed with water at about 25° C. The wash water was collected and analyzed for lactase by ultraviolet spectrophotometry. It was found that less than 1% of the lactase initially charged was washed out of the foam by the wash water. In other words, 99% of the lactase originally charged was bound to the polyurethane foam.

EXAMPLE 11

The washed bound (immobilized) enzyme, which was prepared in Example 10 using 5 mg of lactase, was assayed using a buffered lactose solution. The following method was used:

RUN NO. 1: All of said bound enzyme was placed in a flask containing a quantity of the buffered lactose solution and the rate of glucose formation as a function of time was determined.

RUN NO. 2: Substantially simultaneously a similar run was made in which the bound enzyme was replaced with 5 mg of free (nonbound) enzyme from the same lot that was used to prepare the bound enzyme.

The rates of hydrolysis were identical in Run No. 1 and in Run No. 2 showing that the bound (immobilized) lactase had retained its full activity—i.e., enzyme activity was not lost when the enzyme was bound.

The foam (bound enzyme) was removed from the flask and washed with water. Runs Nos. 1 and 2 (supra) were repeated using the washed foam in the repetition of Run No. 1 and using in the repetition of Run No. 2 a fresh 5 mg portion of free (nonbound enzyme) from the same lot used in original Run No. 2.

The results obtained in these runs (the repetitions of Runs Nos. 1 and 2) were identical with those obtained in original Runs Nos. 1 and 2.

EXAMPLE 12

An isocyanate-capped liquid polyurethane prepolymer was prepared by reacting 31 g of glycerol (glycerine) with an amount of ethylene oxide to form 500 g of an intermediate compound (a hydroxyl-capped polyether) having an equivalent weight of about 500 (i.e., containing about 17 g of —OH group per 500 g of intermediate compound). This intermediate compound was reacted with commercial toluene diisocyanate using 1.05 mole of the toluenediisocyanate per 500 g of the intermediate compound. The resulting isocyanate-capped liquid polyurethane prepolymer was designated "Prepolymer No. 3".

EXAMPLE 13

A 3 g portion of above-described Prepolymer No. 2 (prepared in Example 9) was admixed with 2 ml of benzene and stirred for 5 minutes. The resulting first admixture was then admixed with 10 mg of jack bean urease to form a second admixture which was stirred for 15 minutes at about 25° C. and admixed with water to produce foaming. The admixture was stirred for about 5 minutes.

After foam formation was complete, the self-supporting foam was cut into small pieces (ca. 25 cubic mm each). These small pieces of foam comprising immobilized urease were washed for 18 hours.

A sample of the washed small pieces of foam comprising immobilized urease was assayed for urease activity by comparing the initial rate of ammonia formation obtained where a portion of standard urea solution was hydrolyzed by said immobilized urease with the initial rate of ammonia formation obtained where another portion of said standard urea solution was hydrolyzed by a predetermined amount of free (non-immobilized) jack bean urease.

The results of such assay showed that 11% of the originally charged urease was present in the foam as active immobilized urease.

EXAMPLE 14

The general method of Example 13 was repeated; however, in this instance the benzene was replaced with ethylene glycol.

In this instance an assay of the foam comprising immobilize urease by the general method of Example 13 showed that 3.5% of the urease originally charged was present in the foam in active form.

EXAMPLE 15

The general method of Example 2 was repeated. However, in this instance: (a) the IgG was replaced with 10 mg of urease; and (b) after the admixture of Prepolymer No. 2 and urease had been stirred for 15 minutes, 2 ml of ethylene glycol was added thereto and the resulting composition was stirred for about 5 minutes before adding water (2 g) thereto to produce the self-supporting foam comprising the immobilized (bound) protein—the enzyme urease in this instance.

An assay of the self-supporting foam comprising the immobilized urease according to the general method of Example 13 showed that 21% of the urease initially charged was present in the foam as active immobilized (bound) urease.

EXAMPLE 16

The general method of Example 15 was repeated. However, in this instance the method was modified by: (a) admixing the urease (10 mg) with 2 ml of ethylene glycol; and (b) adding 3 g of Prepolymer No. 2 to the urease-ethylene glycol admixture to form a composition comprising urease, ethylene glycol, and prepolymer. Said composition was then admixed with water as in Example 15 to produce a foam comprising bound (immobilized) urease.

An assay of said foam by the general method used in Example 13 showed that 3.7% of the urease initially charged was present in the foam as active immobilized urease.

The diluent used in Examples 13–16 reduced the viscosity of the isocyanate-capped liquid polyurethane prepolymer. The amount of diluent used is not critical, and reducing the viscosity of the prepolymer frequently makes for ease in operation because the diluted (less viscous) prepolymer is easier to pour and stir. However, the viscosity should not be reduced to such an extent that the prepolymer plus diluent plus protein will fail to produce a self-supporting foam where admixed with water to produce foaming.

EXAMPLE 17

We have found that certain enzymes (e.g., penicillin amidase, glucoamylase, glucose isomerase, and amino acid acylase) which can be immobilized (bound) by the process of our invention exhibit (on the basis of amount of enzyme actually present) lower enzymatic activity in the immobilized foam than in the free (non-immobilized) form.

Although we do not wish to be bound by theory, we believe that this is because such enzymes have primary or secondary amino groups in their (said enzymes') active sites and that such amino groups on some of the enzyme molecules bound to (immobilized on) our poly(urea-urethane) foam comprising the bound (immobilized) enzyme react—where being bound—with isocyanate groups of our isocyanate-capped liquid polyurethane prepolymer to form urea moieties thereby inactivating the active sites comprising such amino groups.

We have found that such decrease in enzymatic activity can be greatly reduced by admixing a so called "substrate" (a material which is acted upon by the particular enzyme (e.g., benzylpenicillin in the case of penicillin amidase, starch in the case of glucoamylase, glucose in the case of glucose isomerase, and an acylated amino acid such as acetylated glycine in the case of amino acid acylase)) with the isocyanate-capped liquid polyurethane prepolymer before admixing the prepolymer with the enzyme to be immobilized.

Run 1, below, where compared with Run 2, below, shows the advantage of this technique.

Run 1

The general method of Example 2 was repeated. However, in this instance: (a) 50 mg of benzylpenicillin was admixed with the prepolymer (Prepolymer No. 2 described in Example 9) before adding the protein thereto; and (b) the protein was 50 mg of penicillin amidase, rather than the IgG used in Example 2.

It was found that 65% of the penicillin amidase charge was bound to the poly(urea-urethane) foam (i.e., 65% of the charged penicillin amidase was immobilized) and 42% of the immobilized penicillin amidase retained its enzymatic activity.

Run 2

The general method of Run 1 was repeated. However, in this instance the addition of benzylpenicillin to the prepolymer was omitted.

It was found that 66% of the charged penicillin amidase was bound (immobilized) but only 14% of the immobilized penicillin amidase retained its enzymatic activity.

In Run 1 of Example 17 the amount of enzyme washed from the foam comprising the immobilized enzyme was determined by spectrophotometry. The difference between this value and the enzyme charged represented the amount of bound (immobilized) enzyme present in the foam.

The amount of immobilized enzyme which retained enzymatic activity was determined by the general method used to determine the activity of immobilized urease in Example 13. However, in this instance the standard urea solution was replaced with standard benzylpenicillin solution and the free (non-immobilized) urease was replaced with free (non-immobilized) penicillin amidase.

The same general method was used to determine: (a) the amount of penicillin amidase bound (immobilized) in Run 2 of Example 17; and (b) the enzymatic activity of the penicillin amidase which was immobilized in said Run 2.

Procedure 1

An isocyanate-capped liquid polyurethane prepolymer (which can be designated "Prepolymer No. P-1") can be prepared by admixing 100 g of ethylene glycol and 561 g of toluene diisocyanate and maintaining the resulting mixture at about 65° C. for about ½ hour.

Procedure 2

The general method of Example 2 can be repeated but modified by replacing the Prepolymer No. 2 used in Example 2 with the above-described Prepolymer No. P-1.

The results will be substantially the same as those obtained in Example 2, except that the washed foam with IgG bound thereto can be designated "Foam A-P".

Procedure 3

The general method of Example 3 can be repeated but modified by replacing Foam A with Foam A-P.

The results will be substantially the same as those obtained in Example 3.

Procedure 4

The general method of Example 5 can be repeated but modified by replacing the Prepolymer No. 2 with Prepolymer No. 1-P.

The results will be substantially the same as those obtained in Example 5.

Procedure 5

A first product can be formed by admixing, in the absence of water, 6 g of toluene diisocyanate and 100 mg of urease. A second product can be formed by admixing, in the absence of water, said first product and 1 g of ethylene glycol. A foam comprising enzymatically active immobilized urease can be formed by admixing the second product and an amount of water effective for producing foaming (e.g., 1 g of water per gram of second product). The resulting poly(urea-ureathane) foam comprising bound (immobilized) urease will exhibit enzymatic activity—i.e.; addition of the foam to an aqueous urea solution (e.g., 0.03 mole of urea per liter) will cause the urea to hydrolyze to form ammonia and carbon dioxide.

Procedure 6

The ethylene glycol used in Procedure 5 can be replaced with an equivalent amount (based on the -OH groups) of a polyethylene glycol having an average molecular weight of 1000 (e.g., PEG 1000). In this instance the results will be substantially the same as those obtained in Procedure 5 (i.e., addition of the foam comprising the immobilized urease to an aqueous urea solution (e.g., 0.03 mole of urea per liter) will cause the urea to hydrolyze).

Procedure 7

A first product can be formed by admixing, in the absence of water, 1 g of ethylene glycol and 100 mg of urease. A second product can be formed by admixing, in the absence of water, said first product and 6 g of toluene diisocyanate. A foam comprising enzymatically active immobilized urease can be formed by admixing the second product an amount of water effective for producing foaming (e.g., 1 g of water per gram of second product). The resulting poly(urea-ureathane) foam comprising bound (immobilized) urease will exhibit enzymatic activity—i.e.; addition of the foam to an aqueous urea solution (e.g., 0.03 mole of urea per liter) will cause the urea to hydrolyze to form ammonia and carbon dioxide.

Procedure 8

The ethylene glycol used in Procedure 7 can be replaced with an equivalent amount (based on the -OH groups) of a polyethylene glycol having an average molecular weight of 1000 (e.g., PEG 1000). In this instance the results will be substantially the same as those obtained in Procedure 7 (i.e., addition of the foam comprising the immobilized urease to an aqueous urea solution (e.g., 0.03 mole of urea per liter) will cause the urea to hydrolyze).

As used herein the term "polyisocyanates" includes diisocyanates.

The isocyanate-capped liquid polyurethane prepolymers used in this invention contain at least two isocyanate groups (reactive isocyanate groups) per molecule of prepolymer.

As used herein the terms "polyurethane foam" and "foamed polyurethane," unless otherwise defined where used, mean a self-supporting poly(urea-urethane) foam. Where formed by the method of our invention in the presence of a protein such foam will comprise the protein in immobilized active form (i.e., the foam will comprise a bound active protein).

Temperature is in degrees centigrade (°C.) unless otherwise defined where used, and percent (%) is expressed in percent by weight unless otherwise defined where used.

What is claimed is:

1. A solution prepared by admixing, in the absence of water, an isocyanate-capped liquid polyurethane prepolymer and a protein, wherein said prepolymer is the reaction product of a polyether polyol with sufficient polyisocyanate to provide at least two free NCO groups per molecule of the prepolymer.

2. The solution of claim 1 in which the isocyanate-capped liquid polyurethane prepolymer is prepared by reacting toluene diisocyanate and a polyethylene glycol.

3. The solution of claim 1 in which the isocyanate-capped liquid polyurethane prepolymer is prepared by reacting toluene diisocyanate and a polyethylene glycol having a molecular weight (average molecular weight) of about 1,000.

4. The solution of claim 1 in which the isocyanate-capped liquid polyurethane prepolymer is prepared by reacting toluene diisocyanate and a member selected from the group consisting of a polyoxybutylene polyol polymer, ethylene glycol, diethylene glycol, a polyoxyethylene polyol polymer, pentaerythritol, glycerol, trimethylolpropane, and a polyoxypropylene polyol polymer.

5. The solution of claim 1 in which the isocyanate-capped liquid polyurethane prepolymer is prepared by reacting toluene diisocyanate with an admixture of a polyethylene glycol having a molecular weight of about 800–1200 and trimethylolpropane, the trimethylolpropane and the polyethylene glycol being provided in a mole ratio of about 1:1–4 and the toluene diisocyanate being provided at a rate of about 0.85–1.25 mole per equivalent of —OH provided by the polyethylene glycol plus the trimethylolpropane.

6. The solution of claim 1 in which the protein is an enzyme, an antibody, or an antigen.

7. The solution of claim 6 in which the enzyme is urease, trypsin, lactase, glucose oxidase, chymotrypsin, ribonuclease, peroxidase, pepsin, rennin, invertase, papain, asparaginase, pectinase, pectin esterase, penicillin amidase, glucose isomerase, lysozyme, amino acid acylase, pronase, alcohol dehydrogenase, α-amylase, β-amylase, subtilisin, amino acid oxidase, catalase, tannase, phenol oxidase, glucoamylase, pullulanase, cellulase, ficin, bromelain, pancreatin, isoamylase, lipase, malic dehydrogenase, hexokinase, lactate dehydrogenase, adenosine deaminase, uricase, galactose oxides, diaphorase, cholinesterase, aldolase, pyruvate carboxylase, phospharylase, cephalosporin amidase, isocitric dehydrogenase, α-glycerolphosphate dehydrogenase, glyceraldehyde-3-phosphate dehydrogenase, malic enzyme, glucose-6-phosphate dehydrogenase, 5-dehydroshikimic reductase, glutathione reductase, glycolic acid oxidase, yeast cytochrome c reductase, luciferase, nitrite reductase, glutamyl transferase, glutathione synthetase, glycocyamine phosphokinase, hippuric acid synthetase, aldehyde oxidase, succinic dehydrogenase, nitrate reductase, xanthine oxidase, lipoyl dehydrogenase, flavin peroxidase, glycine oxidase, carboxylase, α-keto acid dehydrogenase, or transketolase.

8. The solution of claim 6 in which the antigen is human immunoglobulin G.

9. The solution of claim 6 in which the antibody is hepatitis antibody..

10. A process for dissolving a protein comprising admixing the protein with an isocyanate-capped liquid polyurethane prepolymer in the absence of water, wherein said prepolymer is the reaction product of a polyether polyol with sufficient polyisocyanate to provide at least two free NCO groups per molecule of the prepolymer.

11. The process of claim 10 in which the protein is an enzyme, an antibody, or an antigen.

* * * * *